(12) United States Patent
Vinet et al.

(10) Patent No.: US 6,989,233 B1
(45) Date of Patent: Jan. 24, 2006

(54) METHOD AND DEVICE FOR ANALYZING NUCLEIC ACIDS IMMOBILIZED ON A SUPPORT

(75) Inventors: Françoise Vinet, Grenoble (FR); Patrick Chaton, Theys (FR)

(73) Assignee: Commissariat a l'Energie Atomique, Paris (FR)

( * ) Notice: Subject to any disclaimer, the term of this patent is extended or adjusted under 35 U.S.C. 154(b) by 488 days.

(21) Appl. No.: 10/088,522

(22) PCT Filed: Sep. 29, 2000

(86) PCT No.: PCT/FR00/02702

§ 371 (c)(1),
(2), (4) Date: Mar. 29, 2002

(87) PCT Pub. No.: WO01/23866

PCT Pub. Date: Apr. 5, 2001

(30) Foreign Application Priority Data

Sep. 30, 1999 (FR) .................................. 99 12230

(51) Int. Cl.
*C12Q 1/68* (2006.01)
*C12P 19/34* (2006.01)
*C07H 21/04* (2006.01)

(52) U.S. Cl. ..................... 435/6; 435/91.1; 435/91.2; 536/23.1; 536/24.3; 536/24.33

(58) Field of Classification Search ................... 435/6, 435/91.1, 91.2; 536/18.7, 22.1, 23.1, 24.3, 536/24.33; 422/82.05, 82.09
See application file for complete search history.

(56) References Cited

U.S. PATENT DOCUMENTS 5,843,655 A * 12/1998 McGall ......................... 435/6
5,952,654 A * 9/1999 Giese ......................... 250/288

OTHER PUBLICATIONS

K. Adelhelm, et al., "Development of a Sensitive Detection System Based on the Photothermal Effect for Biomolecular Interaction Studies," SPIE Sep. 14, 1995, vol. 2629, pp. 325-333.

* cited by examiner

*Primary Examiner*—Kenneth R. Horlick
*Assistant Examiner*—Young J. Kim
(74) *Attorney, Agent, or Firm*—Oblon, Spivak, McClelland, Maier & Neustadt, P.C.

(57) ABSTRACT

A process for characterizing, quantifying or mapping a nucleic acid or a nitrogenous base fixed on a support by using a photothermal (mirage effect) method. An improved process for manufacturing a nucleic acid biochip on which at least one nucleic acid synthesized in situ is fixed. A device for implementing these processes.

33 Claims, 6 Drawing Sheets

METHOD AND DEVICE FOR ANALYZING NUCLEIC ACIDS IMMOBILIZED ON A SUPPORT

TECHNICAL FIELD

This invention particularly relates to a process for characterization, quantification and mapping of a nitrogenous base, a nucleic acid or a nitrogenous base of a nucleic acid fixed on a support. It also relates to a process for manufacturing a biochip with nucleic acids formed particularly on a solid support on which at least one nucleic acid is fixed, and a device for implementing the process according to this invention.

In general, this invention is used for applications in the fields of chemical or biological analysis systems used for sequencing and studying expression of genes.

For example, these devices may be composed of a set of identical or different molecular probes, for example of nucleic acids fixed on the miniaturized surface of a support or a micro surface. They form what is normally called a biochip, or a DNA chip when the nucleic acid is a deoxyribonucleic acid and an RNA chip when the nucleic acid is a ribonucleic acid. All nucleic acids fixed on the support micro-surfaces form a probes matrix.

During the analysis of a sample using a DNA chip, the target nucleic acids of an extract are marked and deposited on the probes matrix. Hybridisation, in other words matching between molecules of complementary nucleic acids, between probes and marked targets, is used to mark and identify sequences of nucleic acids present in the analysed sample.

Many processes for the manufacture of biochips have been described and developed in recent years to improve miniaturization and the capacity or density of analysis sites on a chip.

Some of these consist of an in situ synthesis of probe nucleic acids on structured substrates. The synthesis method makes use of two different addressing modes to structure the substrate; either a manual addressing mode or a mechanical addressing mode, or a photochemical addressing mode or a mode using lithography techniques.

The first addressing mode is manual addressing using a micro robot or using an automatic synthesiser coupled to the substrate structure. For example, this addressing mode is disclosed in document Southern EM, Nucleic Acid research, Apr. 25, 1994, 22(8): 1368–1373.

A significant improvement to deposition techniques by micro-pipetting using micro robots or jet printing methods makes it possible to envisage industrial processes for the production of probes using chemical synthesis methods. Document WO-A-94 27719 by PROTOGENE LAB INC. and A. P. Blanchard, R. J Kaiser, L. E Hood, Biosensors and Bioelectronics, vol 11, No. 6/7, pages 687 to 690, 1996 discloses use of jet printing techniques to distribute the four basic activated nucleotides of DNA and the coupling reagents, on the different sites of the DNA biochip.

The second addressing mode comprising photochemical addressing techniques and lithography techniques is disclosed for example in Affymetrix, Proc. Natl. Acad. Sci. USA, 1996, Nov. 26; 93(24), 13555–60.

In these two addressing modes, the synthesis uses conventional coupling reactions by means of phosphoramidites or phosphites for successive condensation of judiciously protected nucleosides. The Caruthers document, Science, Oct. 85, page 281, discloses a synthesis cycle comprising deprotection, coupling, capping and oxidation steps. This cycle is a means of making the trace nucleotide grow from the support surface forming the biochip.

Unlike some addressing modes in which the trace nucleotide is presynthesised and therefore purified and qualified before being grafted onto the solid support, the two addressing modes mentioned above require characterization of nucleic acids synthesised after each nucleotide coupling step, since purification is not possible after synthesis.

For example, a synthesis on a solid support in (100×100) $\mu m^2$ sites starting from reagent quantities of a few nl, requires optimisation of the synthesis process in order to obtain a coupling efficiency as close as possible to 100%. The quality of hybridising will depend on the purity of the synthesised probes. Therefore, it is necessary to qualify each synthesis step and to be able to check synthesised sequences.

Furthermore, after carrying out the trace nucleotides synthesis, a check on the probe density and the uniformity of this density over the substrate has to be made.

STATE OF THE ART

The most frequently used method for efficiency calculations for each step is to measure the absorption of dimethoxytrityl cations at 500 nm after deprotection of nucleosides. For example, this method is described in Tetrahedron Letters, vol. 25, No. 4, pages 375 to 378, 1984.

The absorbance to be measured can vary between 0.2 and $10^{-3}$ depending on the quantities of synthesised probes, and this absorption is usually measured by a double beam spectrometer with an absolute precision of the order of 0.1%. There is a sensitivity problem with the characterization instrument necessary for in situ synthesis. If the absorbance measurement is sufficiently precise ($<10^{-3}$), the efficiency can be calculated for each step. This measurement is not specific to a base and therefore cannot give any information about the synthesised sequence. Proportioning of the trityl cation is global for the entire substrate and can be used to calculate an average probe density for each substrate, but it does not give any information about its uniformity.

The document entitled Pease A. C Proc. Natl. Acad. Sci. USA, May 1994, vol. 91, pages 5022 to 5026 discloses a measurement of the fluorescence after hybridisation with marked probes equivalent to the synthesised probes used to determine the sequences. But this measurement is made after the probes have been fully synthesised, and cannot provide any information about the step by step efficiency.

An improvement to this technique has just been proposed by Affymetrix in Glen Mac Gall, J. Org. Chem., 1998, 63, pages 241 to 246. This technique can give an efficiency for each step in the synthesis. Regions of variable lengths of nucleic acids are defined by lithography and at the end of the synthesis, coupling is done with a phosphoramidite containing fluoresceine on all variable length probes.

This method can be used to develop synthesis processes on a solid support, but it cannot characterise the successive steps in grafting trace nucleotides before the end of the complete synthesis of the different trace nucleotides.

The MALDI-TOF (Matrix Assisted Laser Descrption/Ionization Time of Flight) technique disclosed in Little P. D., Anal. Chem. 1997, 69, pages 4540 to 4546, has been used to analyse biochips containing DNA probes. This is the technique that provides the best resolution at the moment for analysis quantities of up to 2.5 fentomoles. Unfortunately, it is destructive and requires a special implementation. Probes must be chemically cleavable at the end of the synthesis and must be co-crystallised with a material capable of absorbing the laser used.

Another technique consists of cleaving the probes after synthesis. They can then be analysed by HPLC (High Pressure Liquid Chromatography). This method can help with the development of synthesis processes on a solid support, but can never be used for characterisation of in situ synthesis on a structured substrate.

DESCRIPTION OF THE INVENTION

The purpose of this invention is to provide a process that is used particularly to qualify each step in the synthesis of a biochip and to verify the sequence of nucleic acids synthesised on the support, and their density and uniformity, the said process overcoming the above mentioned problems encountered with techniques according to prior art, particularly for checking the manufacture of biochips with nucleic acids.

The process according to the invention can be used to characterise, quantify and map a nitrogenous base, a nucleic acid or a nitrogenous base of a nucleic acid fixed on a support. It is characterized in that it consists of characterising, quantifying and mapping the said nucleic acid or the said nitrogenous base by a mirage effect method.

In order to simplify the following description, the term "sample" is used to denote a nitrogenous base, a nucleic acid or a nitrogenous base of a nucleic acid fixed on a support.

For example, nucleic acids and nitrogenous bases are disclosed in the book entitled "Biochimie Générale" (General Biochemistry), J. H. WEIL, $6^{th}$ edition, -MASSON, pages 279–288.

The term nucleic acid used in this description and in the appended claims denotes a chain of nucleotides connected to each other by 3'–5' phosphodiester bonds. The nucleotides are phosphoric esters of nucleosides, and the nucleosides are derived from the bond between a puric or pyrimidic nitrogenous base with a ribose or a deoxyribose. The nucleic acid is a ribonucleic acid (RNA) when the nucleotides forming the nucleic acid contain ribose, and a deoxyribonucleic acid (DNA) when the nucleotides forming the nucleic acid contain deoxyribose. The nitrogenous bases are usually adenine (A), guanine (G), uracile (U) and cytosine (C) when the nucleic acid is an RNA and adenine, guanine and thymine (T) and cytosine when the nucleic acid is a DNA.

The process according to this invention can be used to characterized, quantify and map RNA or DNA nucleic acids, and their nitrogenous bases and their derivatives.

For example, derivatives denote nucleic acids containing derivatives of the above mentioned nitrogenous bases, also called abnormal bases, for example 5-hydroxymethylcytosine derived from cytosine.

This invention also describes a process for manufacturing a nucleic acid biochip formed particularly of a solid support on which at least one nucleic acid synthesised in situ is fixed, the said process comprising at least one synthesis and analysis cycle, including particularly firstly coupling of a nitrogenous base for in situ synthesis of the said nucleic acid fixed on the support, and secondly an analysis to control coupling of the said nitrogenous base, the said analysis being made using a characterisation, quantification or mapping process according to this invention.

Techniques for the in situ synthesis of nucleic acids are described particularly in the above mentioned books disclosing the manufacture of biochips, for example in Caruthers, Science, October 1985, page 281 and subsequent pages. Obviously, coupling of the nitrogenous base corresponds to formation of the 3'–5' phosphodiester bond mentioned above between the nucleic acid being synthesised and the nucleotide containing the nitrogenous base to be coupled.

It is important to note that the thin nucleic acid layers are usually considered as being non absorbent. This is disclosed particularly in "Ellipsometric and interferometric characterization of DNA probes immobilized on a combinational assay", Gray et al., Langmuir 1997, 13, 2833–2842.

Despite this, these inventors have been interested in mirage effect methods, also called photothermal methods.

All these methods use a light source, called a pump beam that is usually a laser modulated at a given frequency, for excitation of the sample for which absorption is to be measured. Part of the incident light energy is absorbed by the sample. The proportion of absorbed energy is fixed by the absorption spectrum for the sample and the emission spectrum of the excitation source. Part of the absorbed energy generates a local temperature gradient that generates an index gradient.

Photothermal methods consist of detecting this index gradient.

The inventors have ingeniously demonstrated that the photothermal deflection method is one of the photothermal methods, or mirage effect methods, that can be used in this invention.

The photothermal deflection method consists of measuring the deviation of a light beam, called a probe beam passing through the area in which the index gradient is located. In other words, it consists of measuring the deviation of the probe beam due to the temperature rise in an absorbent sample by means of the pump beam. This photothermal deflection technique was applied to surface analysis such as absorption mapping, thermal parameter imagery, but not to characterize, quantify and map a nucleic acid or a nitrogenous base of a nucleic acid fixed on a support.

A complete presentation of the photothermal methods, sufficient to implement this invention, may be found for example in the book entitled "Photothermal Spectroscopy Methods for Chemical Analysis, S. E. Bialkowski, vol. 134 in Chemical Analysis: a Series of Monographs on Analytical Chemistry and its Applications, Wiley".

Therefore, in the case of a photothermal deflection method, the nucleic acid or the nitrogenous base of the nucleic acid is illuminated by light originating from an excitation source, and a probe beam is used to detect or measure the absorption, deviation or reflection of light originating from the excitation source by the nucleic acid or by the nitrogenous base.

Figure 1:
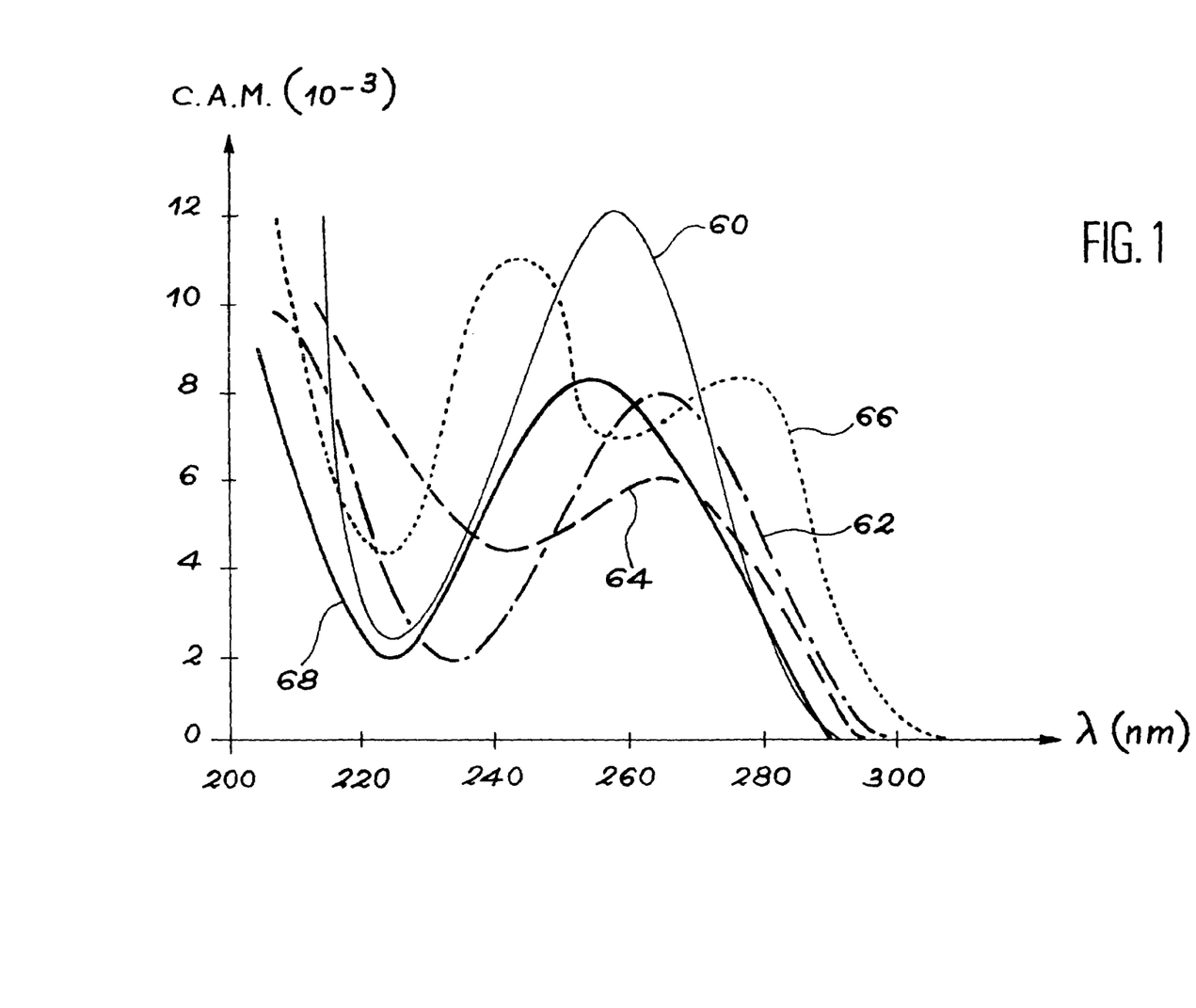
FIG. 1 is a graph that shows the variation of the molar absorption coefficient of G, C, T and A nitrogenous bases, as a function of the wave length.

FIG. 1 appended contains a graph that shows the variation of the absorption coefficient of the A, T, C, G and U bases as a function of the wave length, in order to determine the measurement wave lengths for the process according to this invention. In this figure, the abscissa represents the wave length $\lambda$ in nm and the ordinate represents the molar absorption coefficient (M.A.C.) ($\times 10^{-3}$). Reference 60 indicates the absorption spectrum of adenine (A), and references 62, 64, 66 and 68 indicate the absorption spectra of thymine (T), cytosine (C), guanine (G) and uracile (U) respectively. These spectra can also be used to choose the optimum sensitivity lengths of the DNA or RNA.

According to the invention, the excitation source may for example be a coherent source or an incoherent source.

The role of the pump beam is defined above. For example, it may originate from a pulsed laser, or a continuous intensity modulated laser for which the emission wave length is within the absorption band of nucleic acids. In the case of nucleic acids, the orders of magnitudes of the layer thicknesses are usually a few nanometers.

Therefore according to the invention, the pump beam may be a coherent light, for example a beam of a laser chosen among an argon laser with a wave length of 275 nm, or a solid laser, for example quadrupled YAG with a wave length of 266 nm. According to the invention, absorption may be detected or measured within a spectral range from 200 to 300 nm.

According to the invention, the pump beam may also be incoherent light, for example polychromatic light, if the emission spectrum of the source can give a sufficiently strong signal for detection. For example, incoherent light may originate from a mercury vapour lamp.

The probe beam is preferably directed close to the portion of the sample illuminated by the pump beam. Furthermore, the probe beam may be identical to or different from the pump beam.

According to the invention, the probe beam preferably has a wave length that is not absorbed by the substrate or by the nucleic acids present. The probe beam is preferably a laser beam. For example, it may have a wave length of between 400 to 700 nm. This facilitates alignment with respect to the sample, because the wave lengths are within the visible domain. For example, it may be derived from a helium-neon laser at 633 nm.

The relative position of probe and pump beams defines the configuration used. For example, the probe beam may pass through one or several of the following media—nucleic acids, the solid support or the surrounding medium, for example a liquid or air. The orientation of the probe beam with respect to the pump beam may be chosen at will, for example as a function of the mechanical size and/or to optimise the sensitivity by searching for the maximum absorption as a function of the angle of incidence.

According to the invention, the probe and pump beams can intersect. The position of the intersection point, if any, can also be fixed at will, particularly as a function of the search for the optimum sensitivity. In general, the intersection point is located at the maximum thermal gradient.

Figure 2:
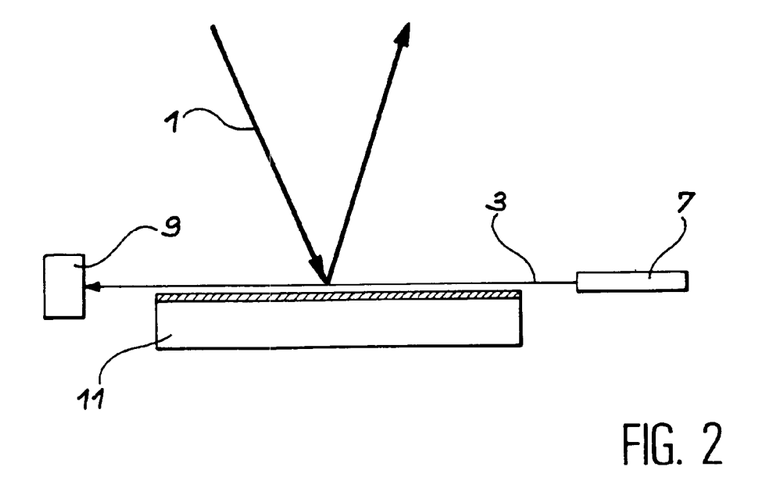
FIG. 2 is a diagram illustrating a photothermal deflection in transverse configuration for the analysis of a sample to be tested using the process according to this invention.
Figure 3:
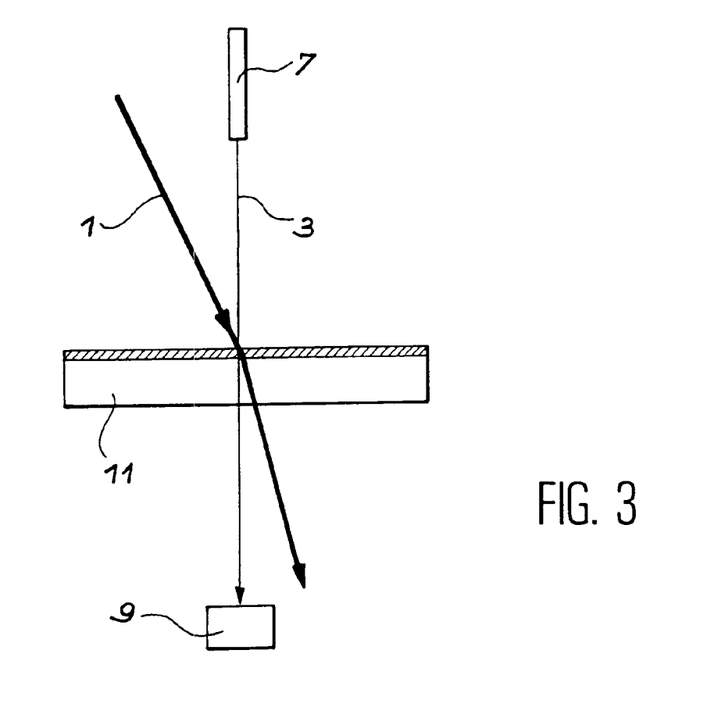
FIG. 3 is a diagram illustrating a photothermal deflection in longitudinal configuration for the analysis of a sample to be tested using the process according to this invention.

According to the invention, the probe and pump beams may be arranged in a transverse configuration or in an approximately collinear configuration. In the transverse configuration, the probe and pump beams intersect and are perpendicular to each other. This configuration is shown diagrammatically in FIG. 2 appended. In the approximately collinear configuration, the pump and probe beams intersect but are almost collinear. FIG. 3 appended is a diagrammatic representation of the collinear configuration.

In these figures, reference 1 indicates the pump beam, reference 3 the probe beam in the transverse configuration, reference 3 indicates the probe beam in the approximately collinear configuration, reference 7 indicates a laser, reference 9 a detector such as a detector with four quadrants and reference 11 indicates the sample consisting of the solid support on which the nucleic acids are fixed.

The reflection or refraction of the probe beam may be detected using a multi-element photodiode, for example a detector with two or four quadrants, a strip or a matrix, or using a simple photodiode, either partially covered by a cache or a blade, or only receiving part of the probe beam.

In the case of a simple photodiode, another detector may be necessary to dissociate variations in the absorption of nucleic acids from variations in the power of the pump beam, if any.

Figure 4:
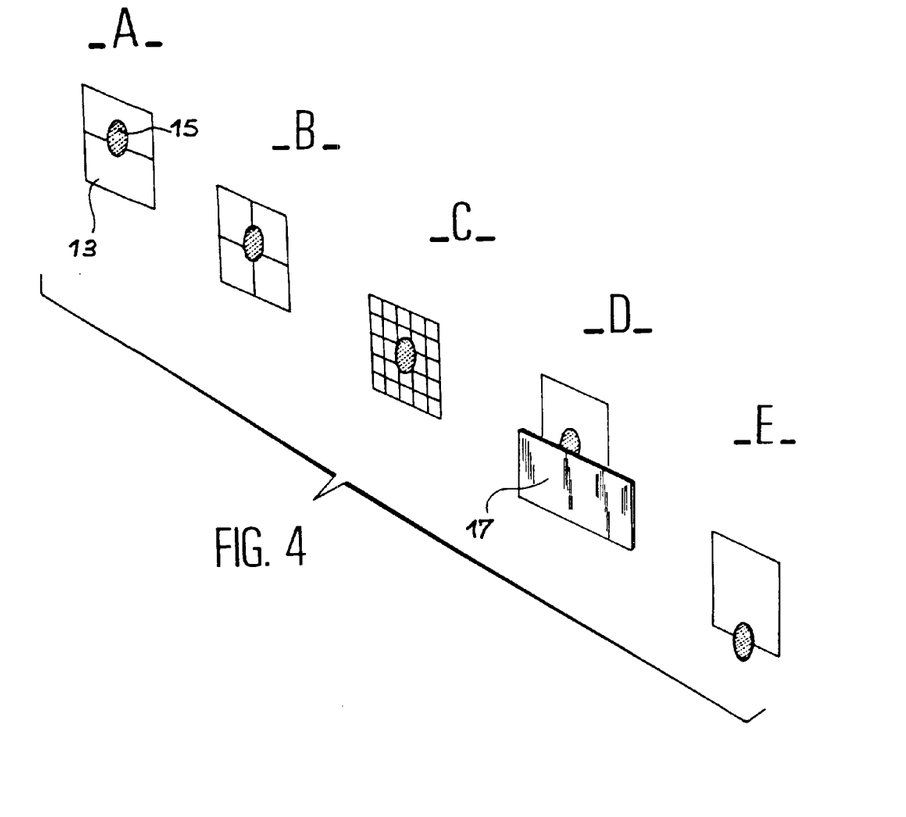

FIG. 4 shows a diagrammatic illustration of different configurations for detection of the deviation of the probe beam; In this figure, -A- diagrammatically represents a bi-quadrant detector 13 and a spot 15 formed by the probe beam on the detector, -B- represents a 4-quadrant detector, -C- represents a matrix detector, -D- represents a simple photodiode partially covered by a cache 17, and -E- represents an off-centred photo detector.

In order to obtain sufficient sensitivity, the deflection of the probe beam induced by the nucleic acid, or the nitrogenous base of the nucleic acid is preferably distinguished from parasite variations due to the medium, such as temperature variations in the laboratory. In order to achieve this, the pump beam may be marked in time, either by a modulation if it is continuous and by its pulse operation. Control of the modulation frequency or the possibility of obtaining a reference signal is a means of preferably detecting reflection due to a temperature rise caused by partial absorption of the pump beam.

Regardless of the configuration of the beams used, the information obtained is local and applies to an area around the impact point of the pump beam on the trace nucleotides or the nitrogenous base.

The size of this area may be fixed by experimental parameters such as the size of the pump beam at the impact point on the sample or its modulation frequency, and by the thermal behaviour of the support, the sample and the ambient medium. This is due particularly to the distribution of heat in the different media.

Since the information is local, the detection instrument may be coupled to a support displacement system onto which the nucleic acids are fixed relative to the pump beam. The assembly can then be used to compare deviation values of the probe beam from one point on the support to another, and in particular the signal may be represented in the form of a map.

Whenever necessary, the deviation signal may be converted into an absorption value, for example by means of a reference sample or a control sample. This control sample, the absorption of which is known and stable, may be the subject of a photothermal deflection measurement under the same experimental conditions as for nucleic acids or nitrogenous bases. For example, the value obtained can be used to calculate a conversion coefficient for the electrical signal measured at an absorption level.

The model of the interaction of the probe beam with the pump beam shows that losses can be measured by absorption of the sample. As we have already seen, the instrument can be calibrated by measuring the deflection signal of a reference sample for which absorption is known in advance. If absorptions are low, it can be shown that the photothermal deflection signal is proportional to absorption of the sample. Therefore, it is possible to work relatively with respect to the reference sample.

With the process according to this invention, losses by absorption of a few ppm ($10^{-6}$) can be measured. The term "losses" refers to the ratio between the power absorbed in the material and the incident light power. One advantageous embodiment of this invention may be to use absorption of the pump beam in P polarisation, in other words parallel to the plane of incidence of trace nucleotides in order to optimise the detection sensitivity. In some cases, absorption in P polarisation passes through a maximum at the Brewster angle of the substrate, for example 56.6° for glass.

Each base has a specific absorption spectrum that can be used. According to this invention, we will follow the variation of the photodeflection signal as a function of the number of bases.

As a first order, the absorption coefficient of an elementary layer is written:

$$A = \alpha e = (4\pi k/\lambda).e$$

where A denotes the absorption of an elementary layer, α denotes the absorption coefficient, e denotes the mechanical thickness, k denotes the thin layer extinction coefficient and λ is the wave length of the pump beam.

After the growth of N bases i, we obtain simply:

$$A = \sum_{i=1}^{i=N} \alpha_i e_i = \sum_{i=1}^{i=N} (4\pi k_i/\lambda) \cdot e_i$$

In the biology domain, this coefficient can also be expressed in the following form:

$$A = \sum_{i=1}^{i=N} \ln 10 \varepsilon_i c_i$$

$\varepsilon_1$ and $c_i$ denote the molar extinction coefficient (1.mol$^{-1}$.cm$^{-1}$) and the concentration (mol.1$^{-1}$) respectively, for each base.

For guidance, extinction coefficients are of the order of $10^{-2}$ to $10^{-3}$ and measurable absorptions are of the order of a few hundred ppm. Therefore, they are weak optical signals.

As a first order of magnitude, steps i are additive on the previous steps. Therefore, the signal is easy to interpret and can be used to monitor the variation of the growth of bases with the steps for in situ synthesis of trace nucleotides.

According to the invention, the support may for example be made of glass, or oxidised silicon, plastic or a gel. For example this support could be a plane support or it could contain micro-cavities, for example micro-bowls.

According to the invention, the first nucleotide may be fixed on the support for in situ synthesis by conventional chemical reactions, chosen firstly depending on the support and secondly so as to fix the nucleotide on the preferred support by a covalent bond. These chemical reactions are disclosed, for example, in Chemistry Letters, 1998, p. 257–258 and Analytical Biochemistry 247, p. 96–101, 1997.

This invention also provides a device for implementation of the process according to this invention, particularly when the method is a photothermal deflection method.

The device comprises the following elements:
a means of positioning the sample comprising a support on which the nucleic acids are fixed,
a means of illuminating the sample,
a means of detecting and/or measuring the absorption, deviation or reflection of light by the sample when it is illuminated by the said illumination means, and
a means of positioning the said illumination means and the said detection and/or measurement means.

According to the invention, the means of positioning the sample may be any known means of precisely displacing the micrometric translation and rotation plates, for example made by MicroCôntrole or Spinder Hoyer. These means may be motor driven to enable automation, particularly for mapping.

According to the invention, the means of illuminating the sample and detecting absorption of light may be chosen particularly as a function of the support and the nucleic acids to be detected. The means of illuminating the sample may for example consist of a pump beam as defined above. The means of detecting absorption may comprise a probe beam and means of detecting refraction or reflection of a probe beam. These means are described below and in the following examples.

According to the invention, the positioning means and the illumination and detection means mentioned above may be means such as those mentioned above for positioning the sample.

Therefore, the invention is innovative particularly due to the fact that a photothermal technique has never been used to characterise, quantify and map a nitrogenous base, a nucleic acid or a nitrogenous base of a nucleic acid fixed on a support. More generally, no method has ever been used based on the measurement of the absorption variation for this type of analysis on support.

In particular, the process according to the invention has the advantage that it does not necessitate any marking step or marker. For example, it may advantageously be used for the manufacture of nucleic acid biochips. Characterisation, quantification and mapping of each nitrogenous base, for example at each in situ synthesis step of a DNA biochip or an RNA biochip, can be used to precisely monitor each step of the said synthesis, and consequently to control the density, the uniformity of the density and the quality of the manufactured biochip and possibly to correct any errors that occur during the synthesis.

This was not possible with techniques according to prior art. Biochips obtained using the process according to this invention are precise, homogeneous and easily reproducible.

The process according to this invention can be used to optimise the in situ synthesis process for trace nucleotides for the manufacture of biochips and to obtain a coupling efficiency equal to or close to 100%; This use will be illustrated in the following examples.

Other elements and advantages of the invention will become clear after reading the description and the examples given below with reference to the appended drawings, obviously given for illustrative purposes and in no way limitative.

BRIEF DESCRIPTION OF THE FIGURES

Other features and advantages of the invention will become clear after reading the following description, in reference to the appended drawings, in which:

FIGS. 4 A, B, C, D and E diagrammatically illustrate different configurations for detection of the deviation of the probe beam;

EXAMPLES

Example 1

Measurement Method

The system used in this example according to the invention is based on photothermal deflection in transverse configuration.

Figure 5:
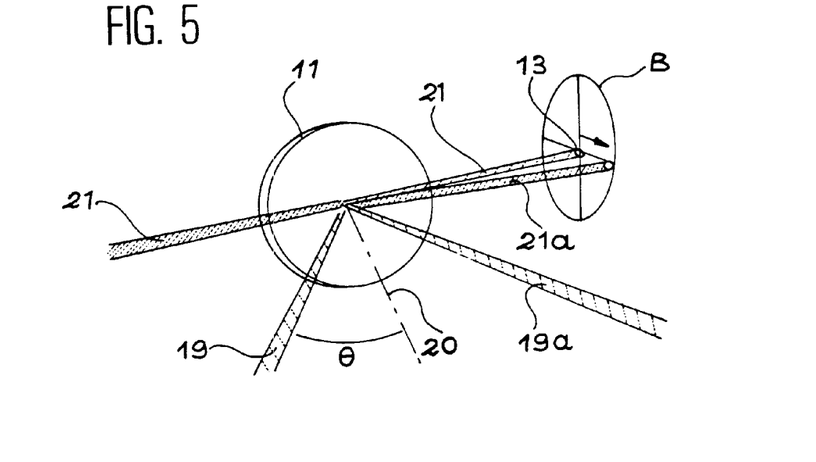
FIG. 5 is a diagrammatic illustration of a measurement of the absorption of a sample using the photothermal deflection method in transverse configuration according to the invention.

FIG. 5 appended is a diagrammatic illustration showing the principle of a measurement of the absorption of a sample composed of a nucleic acid or a nitrogenous base of a nucleic acid fixed on a support by the photothermal deflection method according to the invention.

In this figure, the pump beam 19 is derived from a continuous argon laser at 275 nm (COHERENT INOVA 40) (trade name) (not shown), it is focused on the sample 11 by means of a spherical mirror (not shown), the diameter of the spot (not shown) is about 70 microns at the surface of the sample 11. The wave length of the pump beam is chosen to enable detection of nucleic acids. The power of the pump beam is 300 mW at the laser output.

The probe beam 21 is a probe beam from a helium-neon laser at 633 nm. The wave length of this probe beam is indifferent. According to the invention, a wave length very different from the wave length of the pump beam can give a better signal to noise ratio.

The deflection of the probe beam 21 is detected by means of a four quadrant detector -B- (see FIG. 3) followed by amplification and subtraction electronics (not shown). Reference 21a indicates the probe beam deviated by photothermal deflection. The angle θ indicates the angle of incidence of the pump beam 19 from the normal 20 to the sample (shown in chain dotted lines) and reference 19a indicates the pump beam 19 reflected on the sample.

An interference filter (not shown) selecting the wave length of the probe beam may be placed in front of the four quadrant detector in order to avoid the influence of parasite light originating from the modulated pump beam.

In the device according to this invention, the probe laser, the four quadrant detector and the associated electronics can form an integral part of a commercial measurement cell, for example made by the ALIS Company. The signal output from this cell is sent to a synchronous detection.

The pump beam may be modulated by means of a disk with a mechanical slit, also called a mechanical chopper in the following, the frequency of which is adjustable. The chopper control signal is used as a reference for synchronous detection. The frequency is 157 Hz. The measured signal is obtained at the output from the synchronous detection (amplitude of the deviation signal at the pump beam modulation frequency).

The sample and the two beams are positioned with respect to each other by micrometric translation and rotation plates (made by Micro-Contrôle), some of which are motor driven to enable automation for mapping, for example of a biochip, and in some phases of the adjustment. The adjustments are made automatically to maximise the deflection signal in a plane orthogonal to the sample containing the probe beam. During mapping, a corrective displacement is made if necessary in a direction orthogonal to the map scanning axes in order to guarantee that the relative position is correctly maintained during mapping. This corrective displacement is determined automatically in a preliminary measurement step. The angle of incidence of the pump beam with respect to the normal to the sample and the orientation of the cell with respect to the sample, may be adjustable. The relative positions and orientations of the probe and pump beams may also be adjustable independently.

Figure 6:
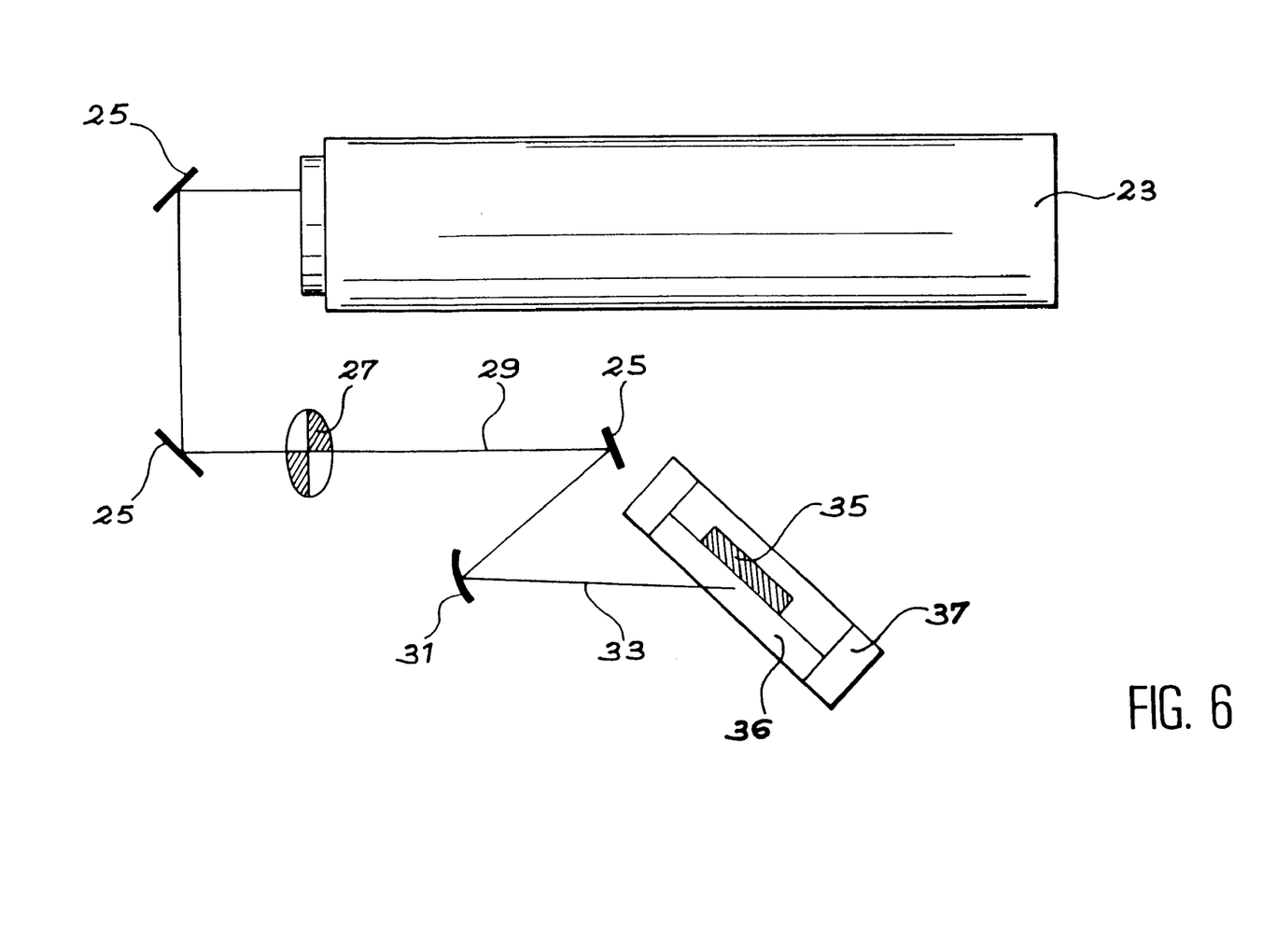
FIG. 6 is a diagram illustrating a device for implementation of the process according to this invention.

A diagram of the device according to the invention is shown in FIG. 6 appended. In this figure, a shutter, not shown on the diagram, interrupts the pump beam during the displacement phases and restores it during a clearly defined time period after a waiting time chosen to allow the set-up to reach a steady state after a displacement. The reference 23 indicates an argon laser at 275 nm, reference 25 indicates laser beam positioning mirrors, reference 27 indicates a mechanical chopper, reference 29 indicates the laser beam after it has passed through the chopper, reference 31 indicates a focusing mirror, reference 35 indicates the measurement sample, reference 36 indicates the probe helium-neon beam and reference 37 indicates the four quadrant photodiode.

For example, the position of the sample may be made repeatable by using a self collimating sight that is not shown on the diagram. The entire measurement device may be controlled by a workstation that controls displacements and acquires deviation signals in two orthogonal directions.

In this embodiment, the deviation is measured along a direction parallel to the plane of the sample and along a direction orthogonal to it. This second direction forms the useful signal. The electronic signal supplied by the synchronous detection may be used as such by comparison between different points on the sample.

It can also be converted into an absorption value by making a reference measurement on a sample considered to be stable in time and under a laser flux, the absorption of which can be measured with a spectrophotometer and which is located in the linearity range of the photothermal deflection measurement bench.

Example 2

In Situ Synthesis of Oligonucleotides on Silica Substrate

The silica substrates used are of the Suprasil type (SESO Company), they have a diameter of 50 mm and are 3 mm thick.

1—Surface Hydroxylation

A solution containing 2 g of soda NaOH/6 ml of deionised water/8 ml of 95% ethanol is prepared and the substrates are incubated in it for 2 hours. The samples are then rinsed with deionised water and dried with a nitrogen blower. This step enables the creation of hydroxyl groups at the surface of the silica (see formula (I) below).

2—Silanisation 2 ml of 3-glucydoxypropyltrimethoxy silane (98%) is put into solution in 7 ml of toluene and 0.6 ml of triethylamine. The samples are put into this solution for one night at 80° C. They are then dried with acetone and nitrogen using a blower and are annealed at 110° C. for 3 hours. The chemical silanisation reaction may be shown diagrammatically as follows:

3—Opening of the Epoxide Function

A solution containing 30 ml of hexaethylene glycol and 18 µm of sulphuric acid is used to enable opening of the epoxide bond and thus to fix hexaethylene glycol. The opening of the epoxide function may be shown diagrammatically as follows:

4—Synthesis of Oligonucleotides

The synthesis of oligonucleotides by the phosphoramidite method is disclosed in document Caruthers, Sciences, October 1985, page 281. it comprises the following steps:

Detritylation, coupling, capping and oxidation.

Detritylation:

The sample is put into 2 ml of a solution containing 3% of trichloracetic acid in dichloromethane (DMT Removal batch 2257-1 Roth) for 2 minutes while stirring. It is then rinsed in dichloromethane and then in acetonitrile and is dried under a pressurized nitrogen jet.

Coupling:

2 ml of a solution containing 25 mg of 2'-deoxy-5'-O-dimethoxytrityl-3'-O— (βcyanoethyl N,N-diisopropyl amino)phosphoramidite is mixed with 150 µm of tetrazole. The sample is put into this solution and stirred under argon for 10 minutes. It is then rinsed in acetonitrile and then dried by a pressurised nitrogen jet.

Capping:

A solution is prepared containing 1 l of CAP and 1 ml of CAP2 (CAP1=acetic anhydride/lutidine/THF, CAP2=1-methylimidazole/THF). The sample is put into this solution for 2 minutes. It is then rinsed in acetonitrile and dried by a pressurised nitrogen jet.

Oxidation:

The sample is put into a solution of 4 ml of Reagent Oxidation (iodine/water/pyridine/THF batch 2254.2 Roth) while stirring for 1 minute. It is then rinsed in acetonitrile in dichloromethane and then in acetonitrile, and is dried by a pressurised nitrogen jet.

These steps are repeated N times, where N is the number of mers of the oligonucleotide to be synthesised. The coupling step determines the nature of the base of each nucleotide (A, C, G, T or U).

Example 3

Absorption Measurement for Different Lengths of Oligomers

This example was made on silica supports as prepared in example 2, with a thickness including 1mer, 2mers and 8mers and with sequences composed of T bases only.

The purpose of this example is to show that the process according to this invention can be used to differentiate the growth of an oligonucleotide base by base.

We made four different samples called Sample 1 to sample 4 using the methods described above. These samples are as follows:

Sample 1: silica/NaOH treatment/silanisation/HEG,
Sample 2: silica/NaOH treatment/silanisation/HEG/synthesis of a monomer comprising a T base,
Sample 3: silica/NaOH treatment/silanisation/HEG/synthesis of a dimer comprising a T base on each nucleotide,
Sample 4: silica/NaOH treatment/silanisation/HEG/synthesis of a octomer comprising a T base on each nucleotide.

1) Measurement Parameters:

Measurements were made using an argon laser.

Wave length 275 mm; 140 mW sample power; chopping frequency F=157 Hz; angle of incidence 45°; detection on two quadrants.

2) Measurement:

Mapping on 1 $mm^2$ at the centre of the samples in steps of 0.1 mm.

For each point X, Y, acquisition of absorption=f(t), where 0<t<4 seconds in time steps of about 100 ms. The acquisition takes place as follows:

for 0<t<1 second by mirage effect: the shutter is closed,
at t=1 second, the shutter is opened,
for 1≦t≦4 seconds: absorption measurement.

The results are given in table I below:

TABLE I

Maximum absorption value (Amax) for each sample

| Sample No. | Sample nature | Amax at 275 nm |
| --- | --- | --- |
| Sample 1 | Silane + HEG | 225 ua |
| Sample 2 | Silane + HEG + 1 T oligo | 280 ua |
| Sample 3 | Silane + HEG + 2 T oligo | 360 ua |
| Sample 4 | Silane + HEG + 8 T oligo | 730 ua | where ua: absorption units.

Figure 9:
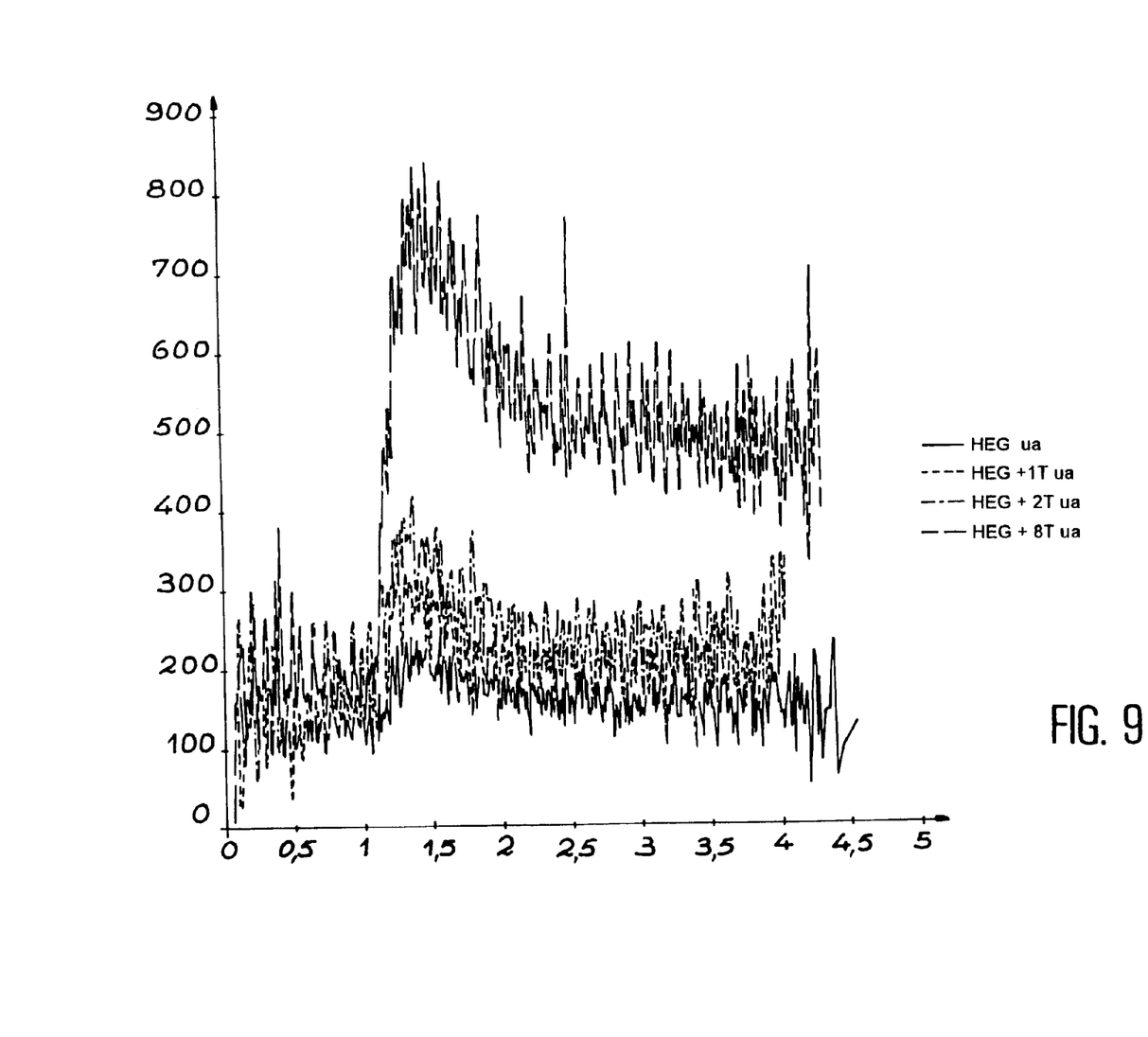
FIG. 9 shows the variation with time of photothermal signals obtained on silica substrates according to this invention.

FIG. 9 appended shows the variation of the photothermal signals as a function of time obtained on silica substrates comprising glycol hexaethylene (HEG), a monomer with one T base (HEG+T), a dimer with two T bases (HEG+2T) and a octomer with eight bases T (HEG+8T).

These curves show the reference (no nitrogenous base), the signal for one T base, two T bases and eight T bases, respectively.

Example 4

Figure 7:
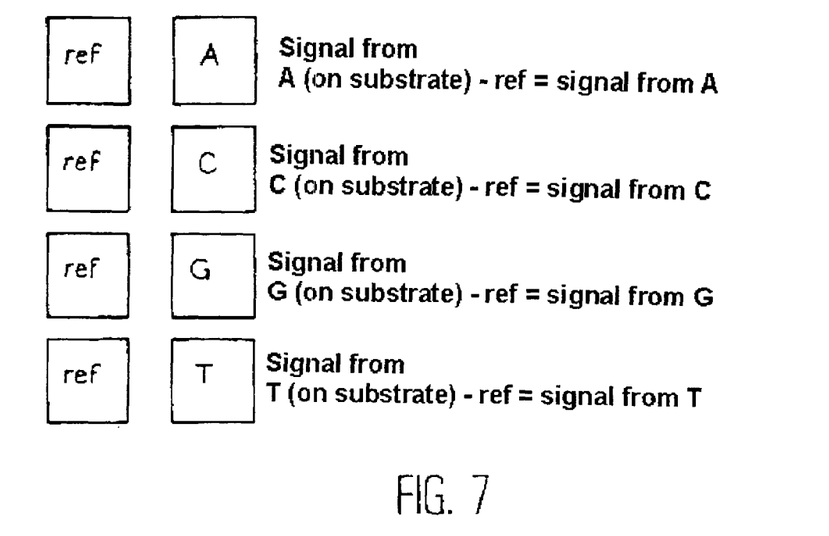
FIGS. 7 and 8 diagrammatically show the method of determining the "image" after each step in the synthesis of a probe using the process according to this invention.
Figure 8:
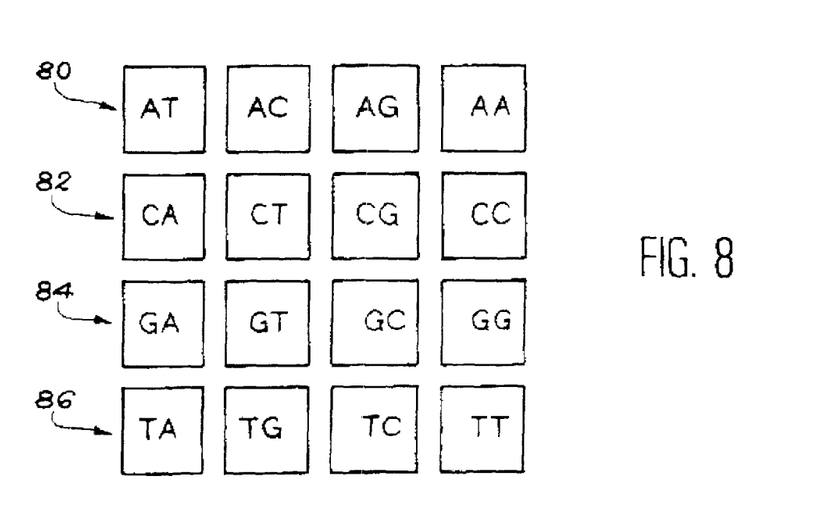

Determination of an Image at Each Step in the Synthesis of an Oligonucleotide The "image" of each synthesis step is determined by comparison with the previous steps. FIGS. 7 and 8 appended diagrammatically show test structures. In these figures, the test structures are shown diagrammatically by squares, or pads, corresponding to areas for example 100×100 $\mu m^2$ in which the optical response will be measured for the substrate (ref), the four bases grafted on the substrates (A, C, G and T) separately, the grafted dimers corresponding to different possible arrangements in the final oligonucleotide (AT, AC, ..., TT).

With these reference pads, we measured the signature of the absorption of each base for the measurement wave length(s). With these absorption measurements, the number of G, C, T, A bases present in the oligonucleotide probe was measured by means of simple subtractions shown in FIG. 7.

As shown in FIG. 8, the signal of each base was calculated regardless of its environment, by making successive subtractions. Thus, in the first line reference 80, the signals of A were determined with respect to A, C, G and T respectively, and in the second line reference 82, the signals of C were determined with respect to A, C, G and T respectively, and in the third line reference 84, the signals of G were determined with respect to A, C, G and T respectively, and in the fourth line reference 86, the signals of T were determined with respect to A, C, G and T respectively.

Example 5

Process for Synthesis of a Biochip According to the Invention

As presented in the description and the above examples, this invention is intended to provide a process for the analysis of each coupling step in the in situ synthesis of oligonucleotides on structured substrates.

The analysis is non-destructive.

However, the inventors have observed that the sample may be damaged above a given power density transmitted to the sample, of the order of 1 kW/cm$^2$.

The invention claimed is:

1. A method for detecting an unmarked molecule(s) fixed on a support, wherein said unmarked molecule(s) is a nitrogenous base or a nucleic acid that has not been marked with a dye comprising:
    illuminating the molecule(s) by light originating from an excitation source or pump beam having a wavelength ranging from 200 to 300 nm, and
    detecting or measuring the absorption, deviation or reflection of light originating from the excitation source by the molecule(s) using a probe beam, thereby detecting said unmarked molecule(s).
2. The method of claim 1, wherein said support is glass.
3. The method of claim 1, wherein said support is oxidized silicon.
4. The method of claim 1, wherein said support is plastic.
5. The method of claim 1, wherein said support is gel.
6. The method of claim 1, wherein said molecule(s) is a nitrogenous base.
7. The method of claim 1, wherein said molecule(s) is a nitrogenous base selected from the group consisting of A, T and U.
8. The method of claim 1, wherein said molecule(s) is a nitrogenous base selected from the group consisting of G and C.
9. The method of claim 1, wherein said molecule(s) is an oligomer comprising two or more nitrogenous bases.
10. The method of claim 1, wherein said molecule(s) is an oligomer or a nucleic acid which has been synthesized on said support.
11. The method of claim 1, comprising detecting or measuring the absorption, deviation or reflection of light originating from the excitation source by a nitrogenous base of a nucleic acid using a probe beam.
12. The method of claim 1, wherein said molecule(s) is a ribonucleic acid.
13. The method of claim 1, wherein said molecule(s) is a deoxyribonucleic acid.
14. The method of claim 1, wherein said molecule(s) is illuminated by a pump beam which is coherent.
15. The method of claim 1, wherein said molecule(s) is illuminated by a pump beam which is incoherent.
16. The method of claim 1, wherein said molecule(s) is illuminated by a pump beam which is an argon laser with a wave length of 275 nm.
17. The method of claim 1, wherein said molecule(s) is illuminated by a pump beam which is a solid laser with a wave length of 266 nm.
18. The method of claim 1, wherein the probe beam has a wavelength ranging from 400 to 700 nm.
19. The method of claim 1, wherein the probe beam is different than the pump beam.
20. The method of claim 1, wherein the probe and pump beams intersect at the maximal thermal gradient.
21. The method of claim 1, wherein the probe and pump beams are arranged in a transverse configuration.
22. The method of claim 1, wherein the probe and pump beams are arranged in an approximately collinear configuration.
23. The method of claim 1, wherein the probe beam passes through the solid support.
24. The method of claim 1, wherein the probe beam passes through the molecule(s).
25. The method of claim 1, wherein the reflection of the probe beam is detected.
26. The method of claim 1, wherein the refraction of the probe beam is detected.
27. The method of claim 1, wherein the absorption of light from the pump beam by the molecule(s) is measured.
28. The method of claim 1, wherein the absorption of light from the pump beam is measured within a spectral range of 200 to 300 mm.
29. The method of claim 1, wherein the absorption of the pump beam parallel to the molecule(s) (P polarization) is measured to optimize the detection sensitivity.
30. A method for synthesizing an oligonucleotide or nucleic acid on a solid substrate, comprising:
    coupling a nitrogenous base to a solid substrate,
    at least one cycle of coupling one or more additional nitrogenous bases to the nitrogenous base fixed to the solid substrate or to the oligonucleotide fixed to the solid substrate to form an oligonucleotide or nucleic acid, and
    detecting the oligonucleotide or nucleic acid synthesized on said substrate by:
        illuminating the molecule(s) by light originating from an excitation source or pump beam having a wavelength ranging from 200–300 nm, and detecting or measuring the absorption, deviation or reflection of light originating from the excitation source by the molecule(s) using a probe beam.

31. The method of claim 30, wherein said synthesizing comprises multiple cycles of coupling a nitrogenous base to a nitrogenous base or oligonucleotide fixed on the support, and said method comprises detecting the nitrogenous based or the oligonucleotide fixed on the support after each synthesis cycle.

32. A method for making a biochip which comprises an oligonucleotide or nucleic acid fixed to a support, comprising:

synthesizing on the surface in situ an oligonucleotide or nucleic acid, and detecting said oligonucleotide or nucleic acid on said surface by:

illuminating the molecule(s) by light originating from an excitation source or pump beam having a wavelength ranging from 200–300 nm, and detecting or measuring the absorption, deviation or reflection of light originating from the excitation source by the molecule(s) using a probe beam.

33. The method of claim 32, wherein said synthesizing comprises at least one cycle of coupling a nitrogenous base to a nitrogenous base or to an oligonucleotide fixed on the support, and said method comprises detecting the nitrogenous base or the oligonucleotide fixed on the support after each synthesis cycle.

* * * * *